Figure 1:
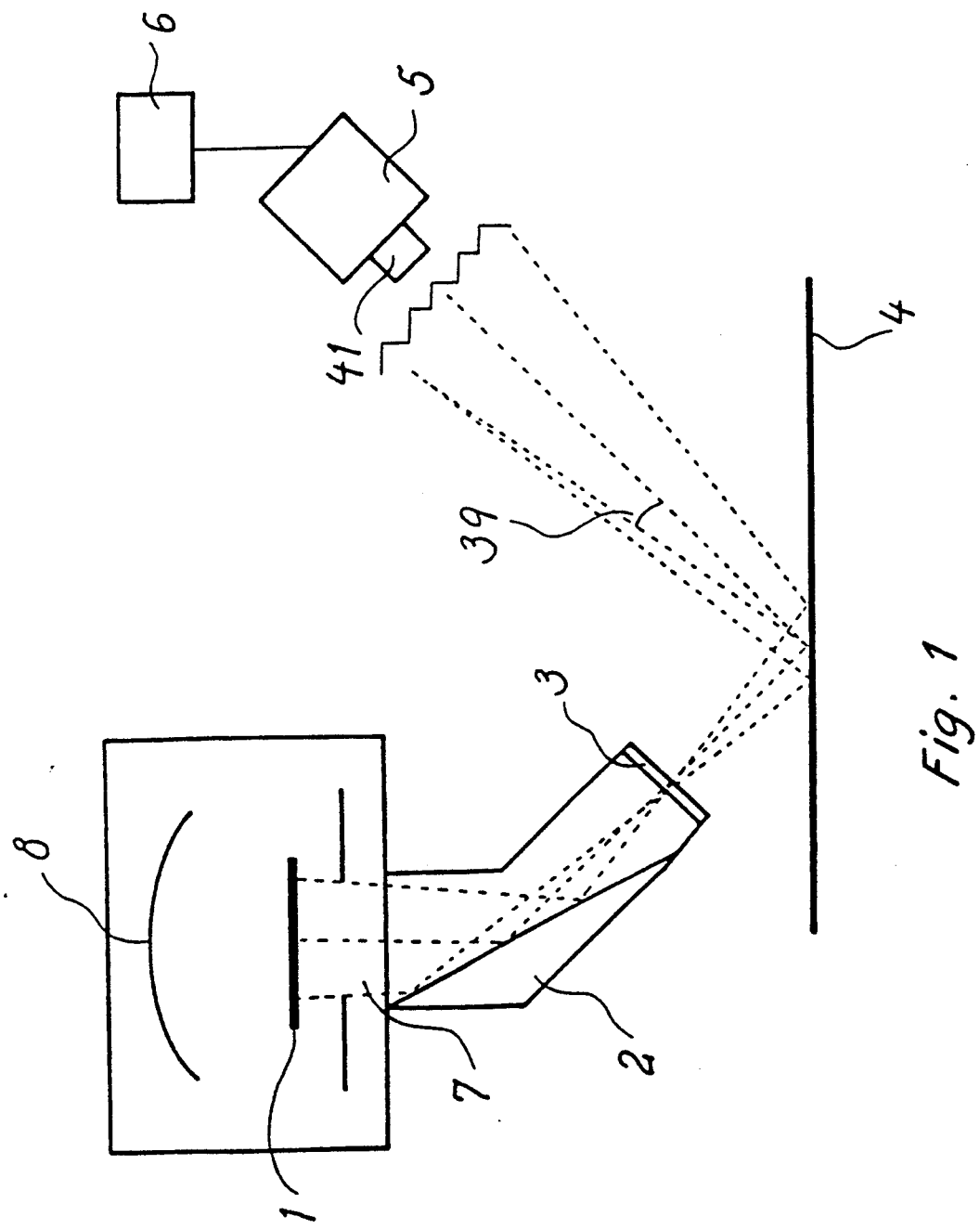

United States Patent [19]
Piironen

[11] Patent Number: 5,018,867
[45] Date of Patent: May 28, 1991

[54] METHOD AND APPARATUS FOR THE INSPECTION OF SPECULARLY REFLECTIVE SURFACES

[75] Inventor: Timo H. Piironen, Raahe, Finland

[73] Assignee: Rautaruukki Oy, Oulu, Finland

[21] Appl. No.: 341,135

[22] Filed: Apr. 20, 1989

[30] Foreign Application Priority Data

Apr. 21, 1988 [FI] Finland .................................. 881857

[51] Int. Cl.$^5$ ............................................. G01N 21/86
[52] U.S. Cl. ..................................... 356/445; 356/429
[58] Field of Search ............... 356/446, 429, 445, 447, 356/448

[56] References Cited

U.S. PATENT DOCUMENTS 4,568,191 2/1986 Barry .................................... 356/446
4,756,619 7/1988 Gerlinger et al. .................... 356/429

OTHER PUBLICATIONS

Scott, B. A., "Instrument for the Measurement of Specular Reflectivity of Bright Metal Surfaces", *Journal of Scientific Instruments*, vol. 37, (Nov. 1960), pp. 435–438.
Melsheimer et al., "Portable Visible-Infrared Reflectometer", Rev. Sci. Instrum, vol. 48, No. 4 (Apr. 1977), pp. 482–483.

Primary Examiner—Richard A. Rosenberger
Attorney, Agent, or Firm—Spensley Horn Jubas & Lubitz

[57] ABSTRACT

A method and apparatus for the visual inspection of at least partly specularly reflective surfaces, such as metal surfaces, which are in continuous motion, by means of a receiver apparatus (5) and an image-analysis apparatus (6). In order to eliminate from the image produced in the received apparatus (5) the uneven illumination caused by variations in the height and orientation of the surface (4) being inspected, the view angle (30) of the received apparatus is adjusted in such a manner that the length of the image of the source of light, formed by means of a perforated lens (3) in front of the source of light (1) is greater than the diameter of the input pupil of the lens of the received apparatus (5).

9 Claims, 3 Drawing Sheets

METHOD AND APPARATUS FOR THE INSPECTION OF SPECULARLY REFLECTIVE SURFACES

The invention relates to a method and apparatus for the automatic visual inspection, by means of a receiver and of image-analysis equipment, of at least partly specularly reflective surfaces, such as metal surfaces, especially those in continuous motion.

U.S. Pat. No. 4,455,090 discloses an apparatus which measures surface properties based on the opacity of a material. The apparatus has an optical projection system for illuminating the sample and a light cell for measuring the light reflected from the sample. The apparatus is intended specifically for the testing of paper, and in connection with a copying paper not containing carbon the apparatus is used for measuring the density of a watermark in the paper in relation to the background. The apparatus according to U.S. Pat. No. 4,455,090 is thus advantageously used for testing material through which light directed to the material can pass at least in part.

U.S. Pat. No. 3,976,382 describes an apparatus for inspecting the geometry of a surface, for example in the treatment of workpieces in the engineering industry. In the apparatus, a source of light transmits light to the surface of the object being inspected. In addition, there is a light-shade disposed between the source of light and the object, the shade producing a sharp boundary surface between the shaded and the illuminated parts of the surface. The thus illuminated part of the object is examined by means of a TV camera, for example. The information thus obtained regarding the geometry of the surface is further used for controlling an apparatus used for altering the geometry of the surface, such as a welding apparatus. According to U.S. Pat. No. 3,976,382, a boundary surface describing the geometry of the surface is obtained of the outline between the shaded surface and the illuminated surface. It is clear that a technique such as this cannot be applied to the inspection of a surface for the purpose of inspecting incidental surface defects in a surface.

U.S. Pat. No. 4,547,073 relates to a surface inspection apparatus and method in which rays of light deflected so as to be parallel are directed by means of a lens onto the polished surface of a silicon wafer. According to the method, defects in the surface of the silicon wafer produce, in the reflected rays of light, rays which deviate from the parallel, in which case surface defects will cause shaded areas in the inspection means. In this case, mere unevenness in the surface of the silicon wafer will produce shaded areas, and therefore the use of the method for surfaces substantially larger than a silicon wafer is not practical.

GB Patent Application 20 20 415 discloses a surface inspection apparatus in which moving bands are illuminated in order to inspect longitudinal grooves in the bands. The apparatus arrangement is disposed in such a manner in relation to the band that the rays coming from the source of light will illuminate the band from both sides of the presumed groove. The apparatus according to GB Application 20 20 415 is thus intended for the examination of surface unevenness known in advance, and thus it is not possible to use the apparatus for detecting unexpected surface defects possibly present within the entire surface area of the band.

The object of the present invention is to eliminate drawbacks in the state of the art and to provide a method and apparatus, better than previous ones, for the visual inspection of specularly reflective surfaces, in which method and apparatus the light coming from at least one source of light and reflecting from the surface being inspected is used for inspecting the obtained image with the aid of light-detecting means and of image-analysis apparatus. The essential characteristics of the invention are given in the accompanying claims.

When the invention is being applied, an image of the core of at least one source of light is produced on the receiver apparatus so that from a flawless specularly reflective surface, such as a metal sheet, the light hits the input pupil of the receiver apparatus, and can be seen as substantially bright in the image on the receiver apparatus. Flawed areas, on the other hand, will scatter light away from the receiver apparatus and are seen in the image as dark areas. According to the invention the length of the image of the core of the source of light in the vertical direction is greater than the diameter of the input pupil of the lens of the receiver apparatus; this allows the view angle of the receiver apparatus to be varied, thereby eliminating from the image any uneven illumination caused by variations of the surface height and surface orientation.

According to the invention, the view angle of the receiver apparatus can be adjusted by altering the length of the source of light or, for example, the adjustable aperture in front of the source of light. It is also possible to place a shade in the adjustable aperture, or substantially in its vicinity, so that the shade preferably covers the central part of the source of light. Thus the shade will prevent direct specular reflection to the receiver apparatus, and by altering the width of the shade it is possible to regulate the view angle of the receiver apparatus in relation to the light specularly reflected from the surface being inspected. Furthermore, by using a shade which divides the light coming from the source of light into two beams of light, it is possible, in the image formed on the receiver apparatus, to compensate for the effect of variations in the evenness of the surface being inspected.

When the invention is being used it is advantageous to have the burning position of the source of light be substantially horizontal, since such a burning position will lengthen the burning period of the source of light. For this reason there is placed between the adjustable aperture and the surface being inspected a mirror by means of which the rays of light coming from the source of light in a substantially horizontal burning position can be directed through a lens, such as a Fresnel lens, onto the surface being inspected and then be reflected in an advantageous view angle to the receiver apparatus.

In the apparatus according to the invention it is also possible to use advantageously a plurality of sources of light and an equal number of lenses in front of the sources of light. In such a case, each source of light is offset in the lateral direction in relation to the lens which corresponds to the source of light, in such a way that each lens will produce on the receiver apparatus an image of one of the sources of light via the illuminated surface. It is possible, when necessary, to use shades between the sources of light to prevent the access of the light coming from a source of light to the adjacent lenses. By using several sources of light and several lenses it is possible to increase the image-forming area inspected or to use smaller-size lenses, the manufacture of which is simpler and less expensive and which are more available than large-sized lenses. Furthermore, in imaging dim scattering surfaces such as steel sheets, a stronger illumination on the surface is obtained than by using one source of light and one lens. By using a plurality of sources of light and of lenses it is, furthermore, possible to control the orientation of the light hitting the surface and thereby improve the visibility of flaws and the evenness of the light.

Figure 2:
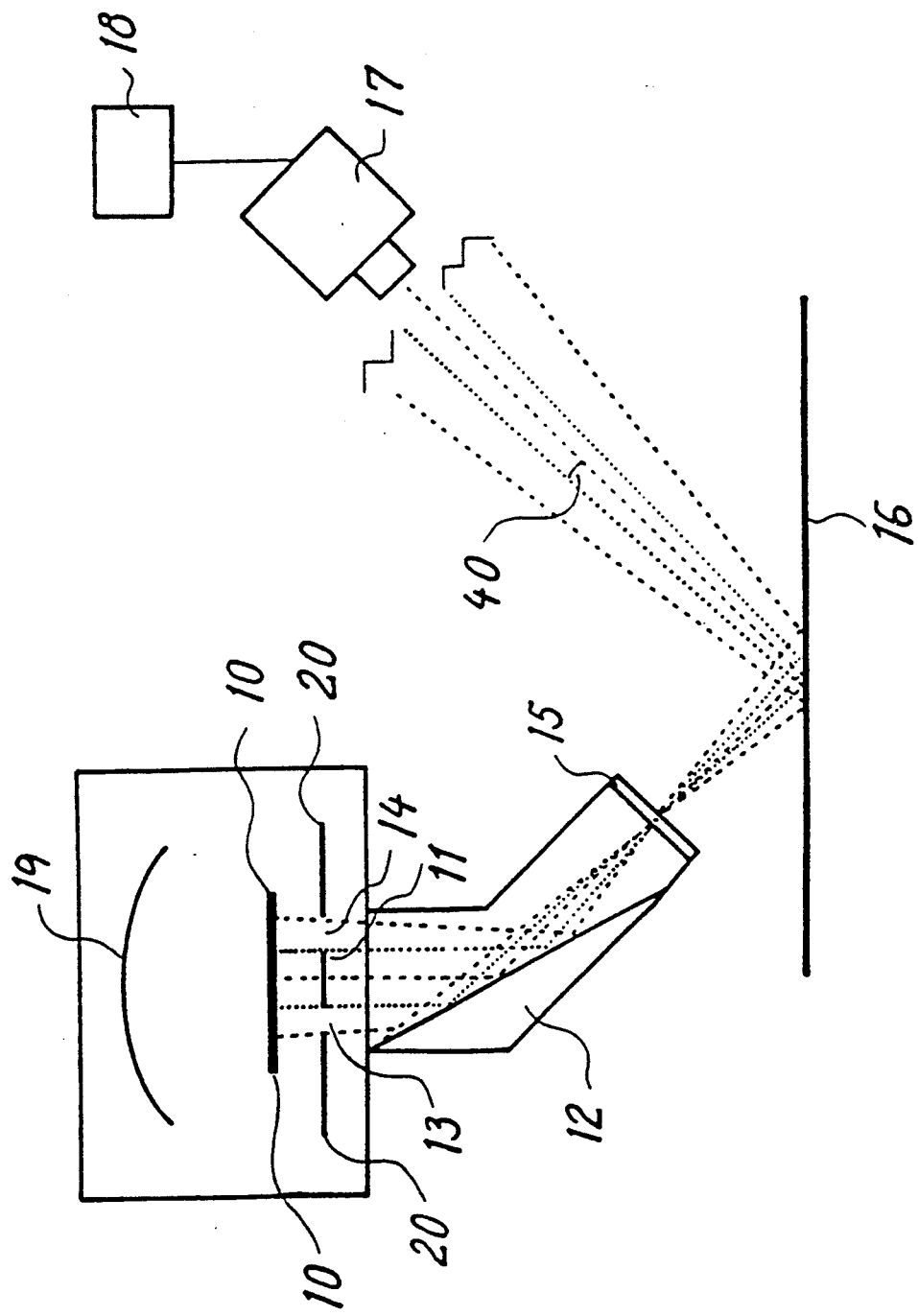
Figure 3:
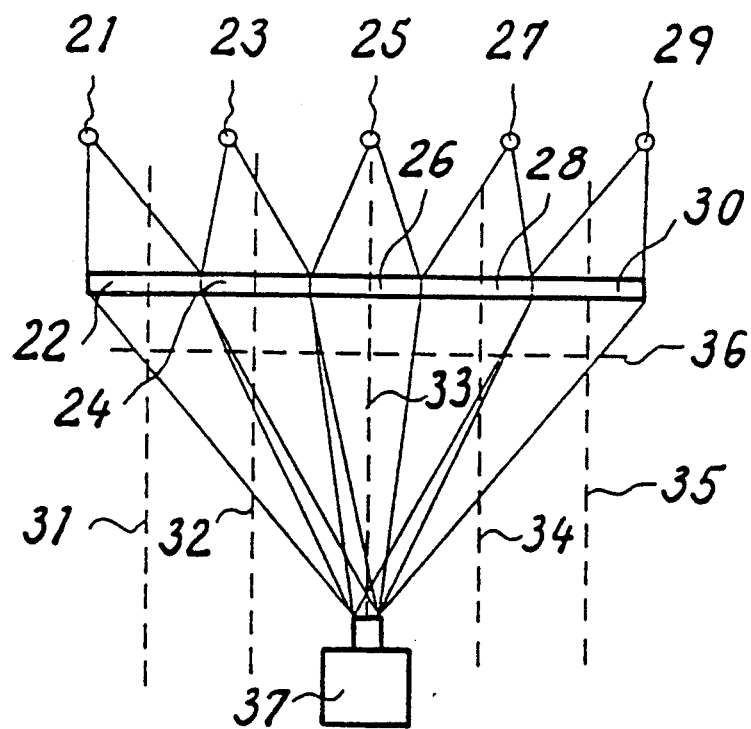

The invention is described below in greater detail with reference to the accompanying drawings, in which FIG. 1 depicts a schematic side elevation of a preferred embodiment of the invention, FIG. 2 depicts a schematic side elevation of another preferred embodiment of the invention, FIG. 3 depicts a schematic plan view of one more preferred embodiment of the invention.

According to FIG. 1, rays of light coming from a source of light 1 are directed to a mirror 2, which deflects the rays of light further through a lens 3 onto the surface 4 being inspected. The rays of light reflected from the surface 4 form the image formed of the source of light 1 by the lens 3, which image is received by the camera 5. The image received by the camera 5 can be further analyzed by means of an image-analysis apparatus 6. According to the invention, the view angle 39 of the camera can be regulated, for example, by adjusting the length of the incandescent bulb serving as the source of light 1, or also by means of an adjustable aperture 7 in front of the source of light 1. FIG. 1 furthermore depicts a curved mirror 8, which is disposed behind the source of light 1 and by means of which it is possible advantageously to increase the luminosity arriving at the input pupil 41 of the lens of the TV camera 5.

In the embodiment according to FIG. 2, there is placed in front of the source of light 10 a shade 11, which divides the rays of light directed to the mirror 12 into two light beams 13 and 14. The light beams 13 and 14 are further directed via a perforated lens 15 onto the surface 16 being inspected. From the surface 16 the light beams 13 and 14 are reflected towards the camera 17 and the image analysis apparatus 18. The magnitude of the view angle 40 of the camera 17 can be regulated advantageously by altering the width of the shade 11. To improve the luminosity of the source of light 10 there is disposed behind the source of light a curved mirror 19 and in front of the source of light limiters 20, which help the regulation of the width of the light beams 13 and 14 produced with the help of the shade 11, and at the same time the adjustment of the view angle 40.

FIG. 3 depicts an arrangement according to the invention in which the light is directed from a plurality of sources of light onto the surface being inspected. In front of the sources of light 21, 23, 25, 27 and 29 there are placed, in a row-like arrangement, perforated lenses 22, 24, 26, 28 and 30, respectively. The optical axes of these lenses are depicted by dashed lines 31, 32, 33, 34 and 35. Of the surface to be imaged, that part which is hit by the rays of light coming from the sources of light and from which they are reflected is depicted by dashed line 36. According FIG. 3, the sources of light 21, 23, 25, 27, 29 are offset in the lateral direction in relation to the optical axes 31, 32, 33, 34 and 35 of the respective lenses so that each lens images one of the sources of light via the illuminated surface onto the camera 37.

I claim:

1. A device for inspecting a reflective surface, comprising:
    a light source,
    a lens for directing light from the light source to the surface,
    light receiving means for receiving light reflected from the surface, the light receiving means comprising a receiver apparatus, an input pupil having a diameter and optics for forming an image of the surface on the receiver apparatus,
    the light source and the light receiving means being disposed so that light directed from the light source to the surface and light reflected from the surface to the light receiving means define substantially equal angles,
    the lens being disposed to form an image of the light source at the input pupil,
    the optics being disposed to form an image of the surface on the receiver apparatus,
    the size of the image of the light source at the input pupil being greater than the diameter of the input pupil.

2. A device according to claim 1, wherein the light receiving means defines an optical axis, further comprising:
    a plurality of substantially parallel light sources,
    the lens being disposed to form an image of the light sources at the input pupil
    the light sources and the lens being aligned with the surface and being disposed substantially perpendicular to the optical axis of the light receiving means,
    whereby the surface is substantially evenly illuminated in a lateral direction.

3. A device according to claim 2, wherein the lens defines an optical axis and wherein each of the plurality of light sources is laterally displaced in a direction substantially perpendicular to the optical axis of the lens.

4. A device according to claim 1, wherein the light source defines an optical axis and comprises a substantially longitudinal light emitting element, the light emitting element being disposed substantially transversely to the optical axis of the light source.

5. A device according to claim 1, wherein light reflected from the surface to the light receiving means comprises a reflected portion and a scattered portion and wherein the light source defines a diameter and a length, further comprising:
    an edge shade for varying the diameter and the length of the light source, whereby the reflected portion and the scattered portion of the light reflected from the surface to the light receiving means are varied.

6. A device according to claim 1, wherein light reflected from the surface to the light receiving means comprises a reflected portion and a scattered portion, further comprising:
    a central shade for delimiting the light reflected from the surface to the light receiving means with regard to the reflected portion and the scattered portion.

7. A device according to claim 6, wherein the light source defines a width and an optical axis and wherein the central shade comprises a strip having a length and a width, the length of the strip being perpendicular to the optical axis of the light source and substantially parallel to the surface, the length of the strip extending substantially the entire width of the light source, and the width of the strip being the measure to be set for producing the delimitation.

8. A device according to claim 1, wherein the light receiving means defines an optical axis and the light reflected from the surface defines an average radiation axis, further comprising:
   a shade disposed between the light source and the surface for adjusting an angle between the optical axis of the light receiving means and the average radiation axis of the light reflected from the surface.

9. A method for inspecting a reflective surface, comprising the steps of:
   providing a light source.
   directing light from the light source through a lens to the surface,
   receiving light reflected from the surface by a light receiving means, the light receiving means comprising an input pupil having a diameter and optics for forming an image of the surface on a receiver apparatus,
   disposing the light source and the light receiving means so that light directed from the light source to the surface and light reflected from the surface to the light receiving means define substantially equal angles,
   disposing the lens to form an image of the light source at the input pupil,
   disposing the optics to form an image of the surface on the receiver apparatus,
   whereby the size of the image of the light source at the input pupil is greater than the diameter of the input pupil.

* * * * *